(12) United States Patent
Glukhovsky

(10) Patent No.: US 7,485,093 B2
(45) Date of Patent: Feb. 3, 2009

(54) DEVICE AND METHOD FOR IN-VIVO SENSING

(75) Inventor: Arkady Glukhovsky, Santa Clarita, CA (US)

(73) Assignee: Given Imaging Ltd., Yoqneam (IL)

( * ) Notice: Subject to any disclaimer, the term of this patent is extended or adjusted under 35 U.S.C. 154(b) by 196 days.

(21) Appl. No.: 10/808,574

(22) Filed: Mar. 25, 2004

(65) Prior Publication Data

US 2004/0181155 A1    Sep. 16, 2004

Related U.S. Application Data

(63) Continuation-in-part of application No. 10/423,023, filed on Apr. 25, 2003, now abandoned.

(60) Provisional application No. 60/375,006, filed on Apr. 25, 2002, provisional application No. 60/457,573, filed on Mar. 27, 2003.

(51) Int. Cl.
*A61B 1/06* (2006.01)
(52) U.S. Cl. .................... 600/160; 600/176
(58) Field of Classification Search .............. 600/593, 600/587, 106–107, 114–117
See application file for complete search history.

(56) References Cited

U.S. PATENT DOCUMENTS

| | | | |
|---|---|---|---|
| 3,683,389 A | 8/1972 | Hollis | |
| 3,971,362 A | 7/1976 | Pope et al. | |
| 4,278,077 A | 7/1981 | Mizumoto | |
| 4,689,621 A | 8/1987 | Kleinberg | |
| 4,741,327 A | 5/1988 | Yabe | |
| 4,844,076 A | 7/1989 | Lesho et al. | |
| 5,279,607 A | 1/1994 | Schentag et al. | |
| 5,604,531 A | 2/1997 | Iddan et al. | |
| 5,819,736 A | 10/1998 | Avny et al. | |
| 5,833,603 A * | 11/1998 | Kovacs et al. | 600/317 |
| 5,984,860 A * | 11/1999 | Shan | 600/116 |
| 6,007,482 A * | 12/1999 | Madni et al. | 600/115 |
| 6,240,312 B1 | 5/2001 | Alfano et al. | |
| 6,719,684 B2 * | 4/2004 | Kim et al. | 600/101 |
| 2001/0017649 A1 | 8/2001 | Yaron | |
| 2001/0051766 A1 | 12/2001 | Gazdzinski | |

(Continued)

FOREIGN PATENT DOCUMENTS

DE    34 40 177    5/1986

(Continued)

OTHER PUBLICATIONS

Robots for the future—Shin-ichi, et al., Nov. 29, 2001.

(Continued)

*Primary Examiner*—John P Leubecker
*Assistant Examiner*—Philip R Smith
(74) *Attorney, Agent, or Firm*—Pearl Cohen Zedek Latzer LLP

(57) ABSTRACT

An in vivo device for sensing a lumen such as the GI tract, such as an in vivo imaging device or other sensing device, may include a substantially spherical housing and an oblong appendage attached to the housing. The appendage may be detached in vivo, for example in the stomach. The in vivo device may then roll and glide along a stomach wall to provide, for example, a smooth sampled image stream.

13 Claims, 6 Drawing Sheets

U.S. PATENT DOCUMENTS

| | | | |
|---|---|---|---|
| 2002/0173718 A1 | 11/2002 | Frisch et al. | |
| 2002/0198439 A1 | 12/2002 | Mizuno | |
| 2002/0198440 A1* | 12/2002 | Snow | 600/116 |
| 2003/0018280 A1 | 1/2003 | Lewkowicz et al. | |
| 2003/0069474 A1 | 4/2003 | Couvillon, Jr. | |
| 2003/0092964 A1 | 5/2003 | Kim et al. | |
| 2003/0181788 A1* | 9/2003 | Yokoi et al. | 600/160 |
| 2003/0195415 A1 | 10/2003 | Iddan | |
| 2003/0214579 A1 | 11/2003 | Iddan | |
| 2003/0214580 A1* | 11/2003 | Iddan | 348/81 |

FOREIGN PATENT DOCUMENTS

| | | |
|---|---|---|
| IL | 143259 | 5/2001 |
| IL | PCT/IL03/01105 | 12/2003 |
| JP | 57-45833 | 3/1982 |
| JP | HEI 3-289779 | 12/1991 |
| JP | 4109927 | 4/1992 |
| JP | HEI 4-109927 | 4/1992 |
| JP | HEI 4-180736 | 6/1992 |
| JP | 5015515 | 1/1993 |
| JP | 2000342522 | 12/2000 |
| JP | 2001224553 | 8/2001 |
| WO | WO 92/21307 | 12/1992 |
| WO | WO 98/11816 | 3/1998 |
| WO | WO 00/22975 | 4/2000 |
| WO | WO 01/08548 | 2/2001 |
| WO | WO 01/50941 | 7/2001 |
| WO | WO 01/65995 | 9/2001 |
| WO | WO 01/87377 | 11/2001 |
| WO | WO 02/094337 | 11/2002 |
| WO | WO 02/095351 | 11/2002 |
| WO | WO 03/009739 | 2/2003 |
| WO | WO 03/021529 | 3/2003 |

OTHER PUBLICATIONS

The Radio Pill, Rowlands, et al., British Communications and Electronics, Aug. 1960, pp. 598-601.

Video Camera to "Take"—RF System lab, Dec. 25, 2001.

Wellesley company sends body montiors into space—Crum, Apr. 1998.

Wang, et al., "Integrated Micro-Instrumentation for Dynamic Monitoring of the Gastro-Intestinal Tract", Presented at IEEE Instrumentation and Measurement Technology Conference, May 2002, Anchorage, Ak, USA, www.see.ed.ac.uk/Naa.publications.html.

Wireless transmission of a color television moving image from the stomach using a miniature CCD camera, light source and microwave transmitter—Swain CP, Gong F, Mills TN. Gastrointest Endosc 1997;45:AB40.

BBC News Online—Pill camera to 'broadcast from the gut', Feb. 21, 2000, www.news.bbc.co.uk.

U.S. Appl. No. 10/213,345, Glukhovsky.

U.S. Appl. No. 10/166,025, Lewkowicz, et al.

www.rfnorkia.com—Norika3, Dec. 24, 2001.

PCT International Search Report of International Application No. PCT/IL03/00339, dated Oct, 6, 2003.

* cited by examiner

DEVICE AND METHOD FOR IN-VIVO
SENSING

RELATED APPLICATION DATA

The present application is a continuation-in-part of U.S. patent application Ser. No. 10/423,023, filed Apr. 25, 2003, now abandoned entitled "Device and Method for Orienting a Device In Vivo" which claims priority from U.S. provisional application Ser. No. 60/375,006, filed Apr. 25, 2002 entitled "Method for Positioning an Object in a Body Lumen" each of which is incorporated herein by reference, and in addition the present application claims priority from addition provisional application Ser. No. 60/457,573, filed Mar. 27, 2003 entitled "In-vivo Imaging Device and Method For In-vivo Sensing".

FIELD OF THE INVENTION

The present invention relates to an in-vivo imaging device particularly suitable for imaging the gastrointestinal (GI) tract or other body lumens.

BACKGROUND OF THE INVENTION

The GI tract may typically be a convoluted long tube that folds many times to fit inside the abdomen, proceeding through the esophagus, stomach, small intestine and large intestine. The upper GI tract includes, inter alia, the relatively narrow esophagus and relatively voluminous stomach area, In-vivo devices, for example, ingestible devices that may move through the GI tract, and that may collect data and transmit the data to a receiver system are known in the art. Ingestible devices that may have an oblong shape, for example, a cylindrical shape with convex domes, generally may move through the GI tract by the natural movement of peristalsis and may be useful for imaging body lumens such as, for example, the GI tact, or other suitable body lumens. In lumens that may be relatively narrow (e.g., esophagus and small intestine), an ingestible device with an oblong shape may progress along an axis of the lumen with little or no tumbling. A wide-angle camera may, for example, scan the entire surface of a lumen. In more voluminous lumens, such as the stomach or large intestine, the movement of an oblong ingestible device may be tumbling and unpredictable, and may, in some cases, not cover the entire surface of the lumen wall. Ingestible imaging and sensing devices that may have a substantially spherical shape, are known in the art, and may generally glide smoothly over a typically moist (and thus substantially frictionless) surface while capturing images, thus possibly avoiding jerky image streams and sensing data captured by the imaging device due to tumbling. There is thus a need for a device, such as for example, an ingestible capsule or other device that may be suitable for effective imaging and sensing of both narrow and voluminous body lumens, such as for example, the esophagus and the stomach area.

SUMMARY OF THE INVENTION

According to an embodiment of the present invention, there is provided an imaging device and a method for imaging the GI tract, in particular the upper GI tract, although other lumens may be imaged. The in-vivo imaging device may be configured to examine both narrow tube like lumens, such as the esophagus and larger, voluminous lumens, such as the stomach, or other body lumens.

According to an embodiment of the present invention, a spherical or substantially spherical shaped imaging device is incorporated within an ingestible device, such as a capsule.

In an embodiment of the present invention, an imaging device may be configured to enable orientation through the esophagus and through the stomach. Other lumens and other parts of the GI tract may be imaged.

BRIEF DESCRIPTION OF THE DRAWINGS

The present invention will be understood and appreciated more fully from the following detailed description taken in conjunction with the drawings in which.

DETAILED DESCRIPTION OF THE INVENTION

Figure 1:
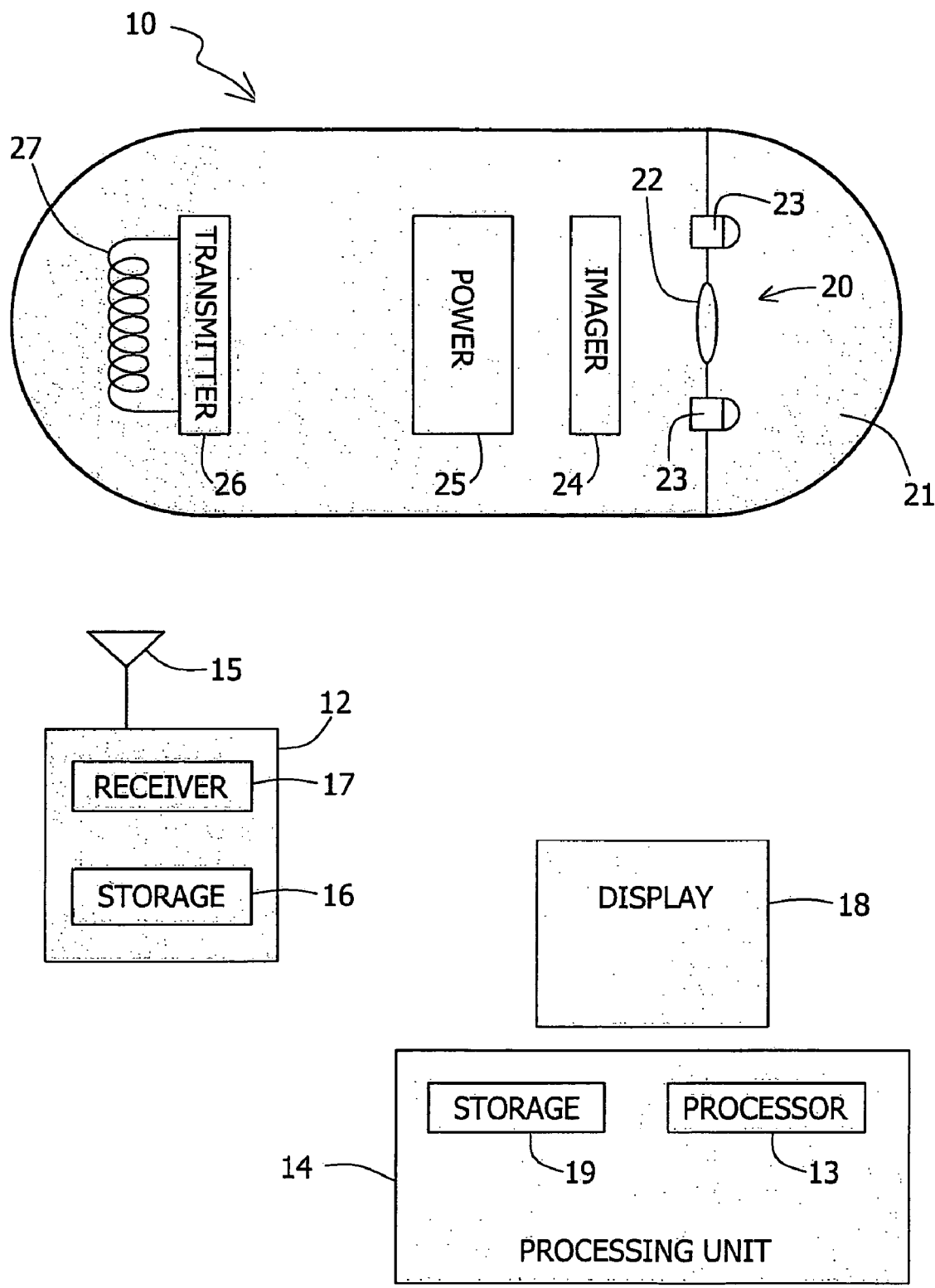
FIG. 1 is a schematic illustration of an oblong ingestible sensing device, according to an embodiment of the present invention.

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

Some embodiments of the present invention are directed to a typically swallowable device that may passively or actively progress through the gastrointestinal (GI) tract, pushed along, in one example, by natural peristalsis. Other embodiments are directed at in vivo sensing devices that may be passed through other body lumens such as through blood vessels, the reproductive tract, etc. The device may be a sensing device, a diagnostic device, a therapeutic device, or a combination thereof. According to one embodiment, the device may include an image sensor. Devices according to embodiments of the present invention may be similar to embodiments described in International Application publication number WO 01/65995, and/or in U.S. Pat. No. 5,604,531, each of which are assigned to the common assignee of the present invention and each of which are hereby incorporated by reference. Devices as described herein may have other configurations and sets of components.

According to some embodiments of the present invention, the device may be configured to change its shape or geometry when entering certain parts of the GI tract, for example voluminous lumens, such as the stomach and/or large intestine, so that it may be better adjusted to movement and sensing through a voluminous body lumen.

According to some embodiments of the present invention, there is provided an in-vivo sensing device, for example, an ingestible imaging device configured to examine both the esophagus and the stomach. Other areas may be examined. According to an embodiment of the present invention, the imaging device may have a spherical or substantially spherical shape for examining, typically but not exclusively, the stomach. Other body lumens may be examined using the spherical shape, for example the colon or other suitable body lumens. In an embodiment of the present invention, the imaging device may have a dissolvable appendage and/or tail or other structure attached to the substantially spherical shaped device. Such an attachable body may, for example, allow the device to maintain an orientation (for example, to progress forward without tumbling) while passing through a relatively narrow body lumen, for example, the esophagus, prior to it reaching a voluminous body lumen, for example, the stomach.

Embodiments of an in-vivo device are described in U.S. Pat. No. 5,604,531 to Iddan et al. and in International Application publication number WO 01/65995, entitled "A Device And System For In Vivo Imaging", published on 13 Sep. 2001, both of which are assigned to the common assignee of the present application and incorporated herein by reference. Embodiments of an substantially spherical shaped in-vivo device are described in International Application number PCT/IL03/01105, entitled "In-Vivo Imaging Device and Method of Manufacture Thereof" assigned to the common assignee of the present invention and incorporated herein by reference. Various embodiments of the present invention may use devices and methods, such as imaging, receiving and/or processing devices and methods, as described in U.S. Pat. No. 5,604,531 WO 01/65995, and/or International Application number PCT/IL03/01105, however other embodiments may use methods and have suitable structures not found in these references.

Reference is now made to FIG. 1, which is a schematic illustration of an exemplary system with an in-vivo device 10, a receiver/recorder 12, and a data processing unit 14 including a processor 13, a storing disk 19, and display 18. The device 10 may in one embodiment of the invention be a capsule, but other configurations may be used. The device 10 may include an optical window 21 and an imaging system 20 for obtaining images from inside a body lumen. The imaging system 20 may include an illumination source 23, such as, for example, a white LED, a sensor, such as an imager 24 that may capture images, and an optical system 22 that may focus the images onto the imager 24. In one embodiment of the invention, imager 24 may be, for example, a complementary metal oxide semiconductor (CMOS) imager. Other imagers may be used, for example a CCD imager or other suitable imagers. The illumination source 23 illuminates the inner portions of the body lumen through optical window 21. Device 10 may further include an ASIC transmitter/controller 26 and an antenna 27 for transmitting data, such as image or video signals captured by imager 24, and a power source 25, such as silver oxide batteries, that may provide power to the electrical elements of the device 10. In another embodiment of the present invention, batteries may not be used and the device may be powered externally. Data from device 10 may be transmitted to an external receiver/recorder 12, for example, worn by the patient for recording and storage. According to one embodiment the receiver/recorder 12 may include a storage unit 16, a receiver 17 and one or more antennas 15. Antenna 15 may be worn the body, for example, on or near the neck throat and abdomen so that signals may be picked up easily. The antenna 15 may be worn, or positioned in other locations or may be embedded in the recorder 12. Recorder 35 may have its data downloaded to a processing unit 14 such as for example a computer, or other processing units for processing and/or displaying output. In one embodiment, the receiver 17 may function as a transceiver and may also transmit signals to the in-vivo device 10. Other components, sets of components, and configurations may be used. In one embodiment of the invention, the device may be an ingestible capsule, but other suitable configurations may be used. Other sensors such as pH or pressure sensors may be used.

The ingestible imaging device 10 may have an oblong shape, for example, device 10 may be a cylinder with convex domes, or have a shape of an oblong ellipsoid, and may be used for capturing images and possibly other data from within a body lumen, such as the GI tract. For an oblong shaped device introduced into a relatively narrow body lumen, for example, the small intestine and the esophagus, the optical axis of the device may maintain a single orientation with respect to the relatively narrow body lumen and may allow continuous smooth imaging of the entire lumen.

In order to examine and image lumens that are relatively voluminous, such as the stomach or large intestine, it may be desirable for the imager to provide a steady image stream of one wall of the lumen at a time. When certain oblong imaging devices move over the surfaces of such lumens, they may, for example, tumble end over end, and thus may produce jerky motion or non-continuous image streams. The image stream captured may, in some cases, lose their optical orientation and thus not provide a relatively steady view of such lumens to be imaged.

Figures 2A, 2B:
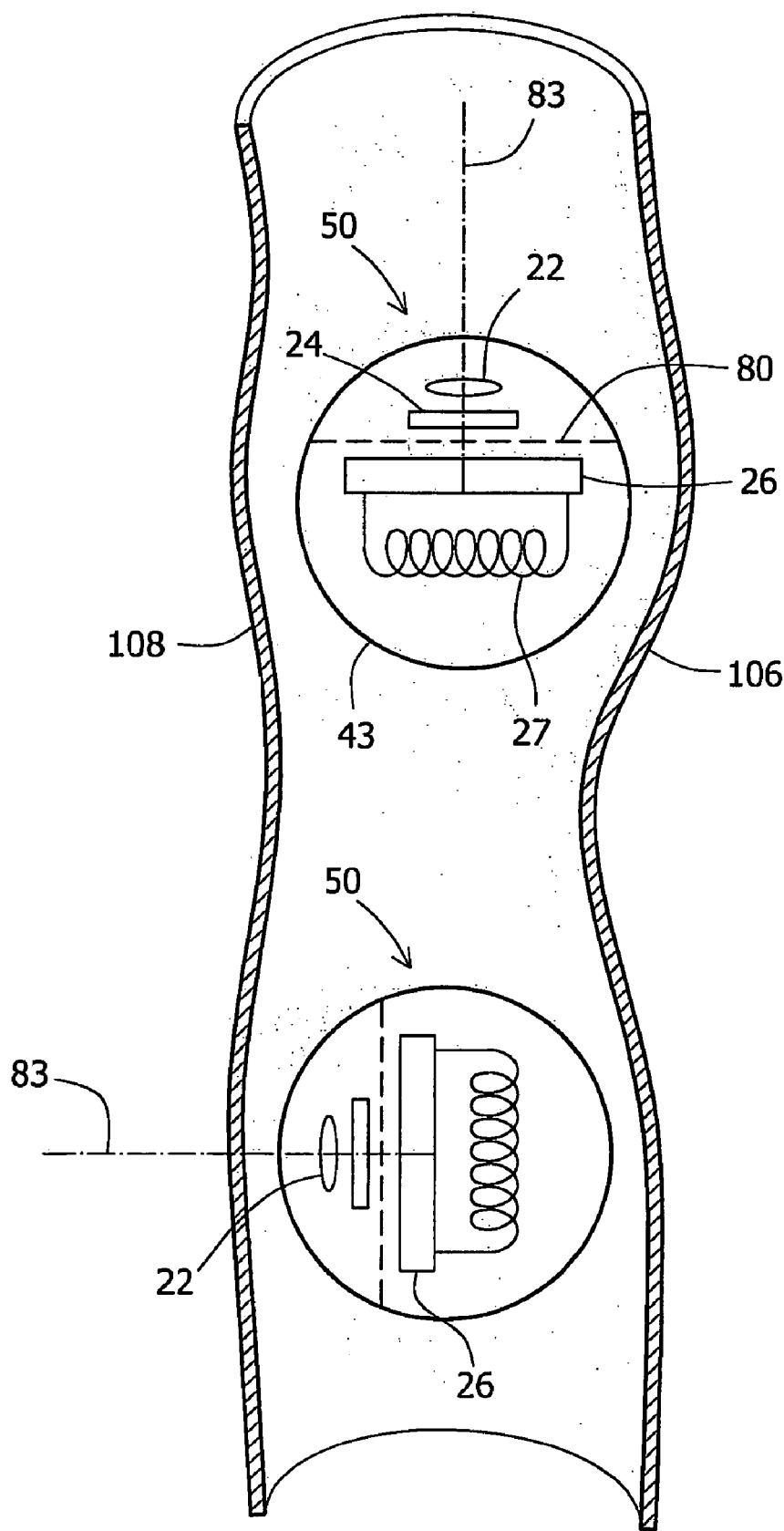
FIGS. 2A and 2B are schematic illustrations of a substantially spherical ingestible sensing devices located in a relatively narrow lumen according to an embodiment of the present invention.

Reference is now made to FIGS. 2A and 2B, that are schematic illustrations of exemplary ingestible devices with a substantially spherical shaped housing. A substantially spherical device 50 may contain similar elements to device 10 which have been similarly numbered. Alternately other elements may be used. For purposes of clarity only a few of the elements are shown. Device 50 may typically be a swallowable device that captures images and other data from within a body lumen, typically the GI tract, and transmits with a transmitter data to an external device such as recorder 12 (such as or similar to that depicted in FIG. 1). A dome 42 may provide a generally transparent cover for the optical elements, may provide a sealed barrier to bodily fluids, and may perform other functions (such as holding optical elements). In one embodiment of the present invention, dome 42 may be an optical dome. A shell 43 may provide a container for components. An upper portion may be separated from a lower portion by, for example, a support 80, which may be, for example, a printed circuit board or plastic board or sheet. Support 80 may be another structure, and components need not be mounted on a separate support. In an alternate embodiment such a separation need not be performed.

When used herein, upper and lower are relative terms, to be used interchangeably as per the context. The portions may not evenly split the device 50. Alternatively, the viewing window may be, for example a ring shaped viewing window.

Typically, the outer shape of the device 50 (which in the embodiment shown may be formed by dome 42 and shell 43, but may be formed by other components) may be spherical or substantially spherical. When used herein, "spherical or substantially spherical" may be defined as a geometrical shape having a diameter r and a longitudinal axis L wherein $r<=L<=1.5r$. When L is approximately 1.5r, the shape may be ellipsoidal or cylindrical shaped. In one embodiment r may be about 11.4 mm; however, other dimensions may be used. Note that, as device 50 may be rotated about an axis, different cross sections of the device 50 may differ; for example, the device 50 may be a somewhat irregular sphere or ellipsoid. The shape of the device 50 may differ when viewed from different angles.

Typically, device 50 includes at least one sensor such as an imager 24, for capturing images (and possibly other sensors, such as a temperature sensor, a pH sensor, a pressure sensor, etc.). A set of illumination source(s), (where a set may include one item) such as, for example, a set of white LEDs (other elements may be used) may be used to illuminate an area for viewing. An optical system 22, may include, for example, one or more optical elements, such as one or more lenses or composite lens assemblies, one or more suitable optical filters, or any other suitable optical elements, may aid in focusing reflected light onto the imager 24 and performing other light processing. The optical system 22 may be mounted on an optical isolation element. Other systems or methods for positioning a lens(es) or other suitable optical elements may be used. In one embodiment, the field of view may be 80-90 degrees; other fields of view, such fields of views that are larger than 90 degrees, for example, 140 degrees may be used. The focus range is typically between 0 to 40 mm; other suitable distances may be used. Device 50 typically may include a transmitter 26 and antenna 27, for transmitting images and other (e.g., non-image) information to a receiving device, and may include other components, such as, for example, a compression module, for compressing data. The transmitter 26 may typically be an ultra low power radio frequency (RF) transmitter with high bandwidth input, possibly provided in chip scale packaging. Other suitable transmitters may be used. The transmitter 26 may also include circuitry and functionality for controlling the device 50. Transmitter 26 may be, for example, an ASIC, a typically generalized integrated device that may include transmitting and/or receiving capabilities, a controller, drivers for the LED's and a variety of other mix of analog and digital elements, "computer on a chip", micro controller, etc., or other component. Typically device 50 is powered by an internal power source such as a battery but may also be configured to receive energy from an external source.

FIGS. 2A and 2B schematically illustrate a spherical device 50 traveling through a narrow lumen, such as for example the esophagus 52. Device 50 may be, for example, a capsule, but may have other configurations. As shown in FIG. 2A, the optical axis of the spherical device 50 may be substantially parallel to the sides of the lumen wall 106 and 108 allowing for imaging of the walls of the lumen. However, since the device is spherical, the device may rotate relatively easily without expanding the local diameter of the lumen. As may be seen in FIG. 2B, the optical axis 83 of the spherical device 50 may be perpendicular to that of FIG. 2A, which allows only one of the walls 108 of the lumen to be viewed, thus leaving parts of the intestinal wall not imaged.

Figure 3A:
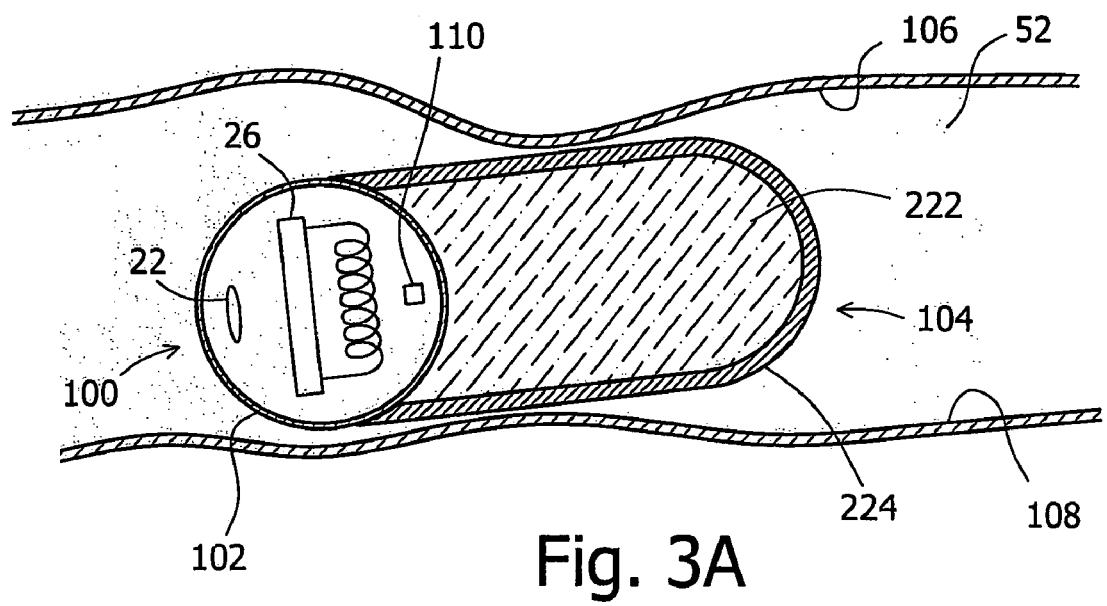
FIGS. 3A and 3B are schematic illustrations of an ingestible sensing device constructed and operative in accordance with embodiments of the present invention.

Reference is now made to FIG. 3A, which is a schematic illustration of an in-vivo device 100 with a sensor and transmitter enclosed within a spherical housing 102 and a detachable appendage 104. Device 100 may be, for example, an ingestible device, constructed and operative in accordance with an embodiment of the invention. Ingestible device 100 may include a generally spherical housing 102 and a detachable appendage 104, together forming a generally ellipsoidal or cylindrical with convex dome shape; note other suitable shapes or configurations may be used. According to one embodiment, housing 102 may be configured to withstand passage through the GI tract without deterioration. The spherical or substantially spherical housing 102 may be configured to contain a sensor, such as, for example, an imaging system for obtaining images from inside a body lumen via an optical window. The spherical housing 102 of the ingestible device 100 may contain similar elements to device 10 and/or spherical device 50. In alternate embodiments other suitable elements may be used. Similar elements have been similarly numbered. For the purposes of clarity, only a few of the elements of the in-vivo sensor are shown. The housing 102 may be composed of material such as plastic. Device 100 may transmit data to a recorder 12 that may be later downloaded to a processor 14 and displayed on a display 18 (FIG. 1). Other suitable configurations may be used.

Device 100 typically may be or may include an autonomous swallowable capsule, but device 100 may have other shapes and need not be swallowable or autonomous. Embodiments of device 100 are typically autonomous, and are typically self-contained. For example, device 100 may be a capsule or another unit where all the components are substantially contained within a container or shell, and where device 100 does not require any wires or cables to, for example, receive power or transmit information. Device 100 may communicate with an external receiving and display system to provide display of data, control, or other functions. For example, power may be provided by an internal battery or a wireless receiving system. Other embodiments may have other configurations and capabilities. For example, components may be distributed over multiple sites or units. Control information may be received from an external source.

The oblong appendage 104 may be disintegrable or may include a disintegrable attachment mechanism. According to one embodiment the oblong appendage 104 remains intact while passing through, for example, the esophagus but may degrade or detach when it reaches, for example, the stomach. According to one embodiment, the degradation may be time dependent. According to another embodiment the detachment or degradation may be externally triggered or controlled by, for example, a recorder 12 or other unit, or may be dependent on other parameters, such as on environmental parameters, for example, pH, temperature, enzymatic activity, or other suitable parameters. The oblong appendage 104 may be composed of material that may have a tendency, in, for example, an aqueous environment, to dissolve over a relatively short period of time, for example, a few minutes, which may typically be the time it takes for the device 100 to pass through the esophagus into the stomach. Other suitable periods may be used. Examples of such a dissolvable material may be gelatin, lactose, poly ethylene glycol, or pressed powder covered with parylene, e.g., parylene C. According to another embodiment the oblong body may be composed of pH sensitive material. Thus, when the device 100 moves from the environment of, for example, the esophagus into, for example, the acidic environment of, for example, the stomach, the appendage 104 may dissolve leaving the spherical housing 102 to view the stomach lumen. According to yet another embodiment, the appendage 104 may be composed of material such as a thermo-responsive hydrogel that can cause the appendage 104 to dissolve in a typically warm or typically cold environment. In this case, a patient may be made to swallow device 100 and shortly after swallowing the device 100, the patient may, for example, intake a warm or cold drink that may cause elevated or reduced temperatures in the stomach and subsequent disintegration of appendage 104. Other suitable methods of changing temperatures or of triggering detachment or disintegration of appendage 104 may be used.

According to some embodiments, the appendage 104 may include, for example, an outer coating 224 and an internal filling 222. According to one embodiment, the outer coating 224 may be a layer of strong, semi-permeable material that may encapsulate the internal filling 222 and may control the diffusion rate of substances diffusing into appendage 104 and/or out from appendage 104. The internal filling 222, may maintain, for example, an osmolarity that favors the inward or outward diffusion of ions, such that the internal filling 222 may swell or be depleted (and exchanged for endo-luminal liquids) in a process that may preferably be determined by the properties of the internal filling 222 and the rate may preferably be limited by the properties of the outer coating 224.

In one embodiment, the outer coating 224 may be made of, for example, a parylene C coated hydrogel polymer, such as, for example, ethyl cellulose acetate and the internal filling 222 may include, for example, filler, preferably a biodegradable polymer, such as, for example, polymer of lactide and golycollide (PLGA). In alternate embodiments, other suitable materials may be used. Parylene C, that may be a dimer of poly p-xylene with a substitution of a single chlorine molecule, may provide a combination of properties such as, for example, a low permeability to moisture, chemicals, and other corrosive gases. The hydrogel polymer may create a matrix that may contain the filler and that may be strong enough to withstand endo-luminal pressure. The filler may absorb liquid from the body lumen environment that may seep, for example, through the hydrogel matrix at a rate that may typically be determined by the osmotic gradient between the endo-luminal environment and the inner filling and by properties of the parylene C coating and of the hydrogel polymer, such as, for example, by the extent of the hydrogel polymer cross linking, its concentration, its thickness and so on. The filler may swell and after a period of time, for example, starts pressing against the outer coating 224. The internal pressure may rise as more liquid may be absorbed. When the pressure reaches a certain, predetermined point the hydrogel matrix and the parylene C coating may rupture and the appendage 104 may essentially be degraded.

In another embodiment, the outer coating 224 may be, for example, a low solubility material that may be permissive to an inward flow of endo-luminal liquids or, for example, a soluble material that may initially be impermeable to endo-luminal liquids but may become permeable as it is dissolved, due to thinning of the layer. The inward flow of endo-luminal liquids may, for example, causes the pressure in the appendage 104 to be elevated and ultimately the outer coating 224 may be ruptured, thereby diminishing the dimensions of the appendage 104. For example, in a appendage 104 having a diameter, for example, of 11 mm, a layer of parylene C, for example, a few micrometers thick (e.g., 5-20 micrometers, although other suitable thicknesses may be used) may be used as the outer coating 224 and, for example, a 11 mm thick filling of any suitable filler may be used as the internal filling 222. The thickness of the outer coating layer 224 may serve, for example, to regulate the rate of the inward flow of endo-luminal liquids. In another embodiment the outer coating 224 may be made of, for example, a 10-micrometer thick layer of parylene C and a 0.5 nm thick layer of gelatin. Other suitable dimensions may be used. The gelatin, that may be, for example, soft, hard, or vegetable gelatin, may be cross-linked to, for example, increase its durability. In an alternative embodiment the osmolarity of the internal filling may favor a diffusion of ions into the body lumen, a gradual depletion of the internal core and a flow of liquids into the device. The depleting internal core is exchanged for liquids, that may exert pressure on the device coating, and after a predetermined point the outer coating may rupture leading to disintegration of the appendage 104. The dimensions and thicknesses given are by way of example only; other suitable dimensions and thicknesses may be used. Thus, an appendage 104 according to an embodiment of the invention may be designed to disintegrate at a desired rate.

According to other embodiments the internal filling 222 may include different hydrogel fillings, which may be induced to go through a change of swelling. For example, a thermo-responsive hydrogel may be stimulated by a change in temperature to go through polymer-polymer and water-polymer interactions that may result in a change in swelling of the hydrogel. Likewise, an acidic or basic hydrogel may be induced by a change in pH. The swelling of modified hydrogels may also be stimulated. For example, a hydrogel containing electron accepting groups may be stimulated by the presence of electron donating compounds, a poly electrolyte hydrogel may be stimulated in the presence of an applied electric field and magnetic particles dispersed in microspheres, such as alginate microspheres, may be stimulated in the presence of an applied magnetic field. Thus, the disintegration of an appendage 104, according to an embodiment of the invention, may be caused or triggered to degrade or externally controlled, for example, by artificially changing the endo-luminal temperature or pH or by externally applying an electric signal or magnetic field to the body lumen. According to yet further embodiments, the appendage 104 may be caused to degrade or made of materials that may be degradable by external methods such as by, for example, ultrasound or other suitable methods.

Other dimensions and other suitable substances may be used. The appendage 104 may be manufactured and shaped by any suitable method such as by molding, pressing, extruding, etc.

Figure 3B:
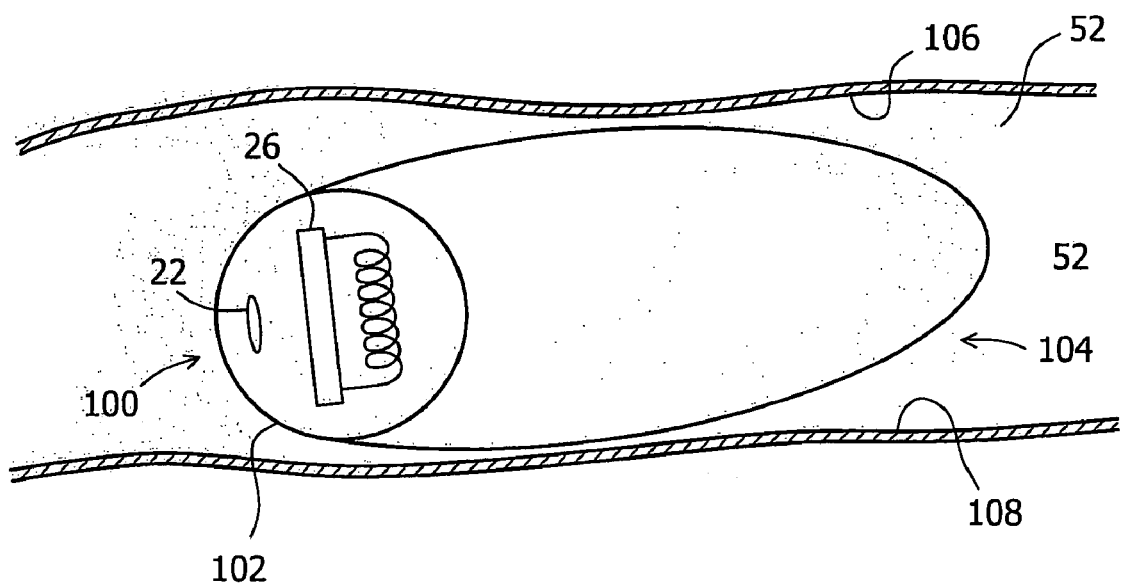

Thus, as may be seen in FIG. 3A, the overall shape of the device 100 (as viewed longitudinally) may be generally ellipsoidal and/or cylindrical since the attachable appendage 104 may determine the shape of the device prior to disintegration of the attachable appendage 104. Of course, other suitable initial shapes may be used. According to one embodiment the dimensions of the device 100 may be, for example, 11 mm×26 mm whereas the housing 102 may be typically spherical, but may possibly have other suitable shapes. Reference is now made to FIG. 3B schematically showing a device 100, with a spherical sensing device 102 attached to an oblong appendage 104, together forming a generally ellipsoidal shape device 100. Sensing device 102, in one example, may have a diameter of, for example, 12 mm and the appendage 104 may have, for example, a maximum cross sectional diameter of 14 mm, however other suitable shapes and other suitable dimensions may be possible. Thus, initially, for example, just after swallowing, the spherical housing 102 may be prevented from rotating in at least some directions (because of the attached appendage 104) and the optical axis of the orientation of the imaging system may be maintained along the lumen of the esophagus, allowing for imaging of both walls 106 and 108 of the esophagus.

According to one embodiment, appendage 104 and spherical housing 102 may be attached by any suitable attaching device or substance such as, for example, glue. The glue may be any dissolvable glue, for example, UV glue or other known dissolvable glues. Alternatively spherical housing 102 may be molded into elliptical and/or cylindrical appendage 104. Other suitable methods of attaching spherical housing 102 and appendage 104 may be used, such as mechanical attaching methods, clamping, fasteners, etc.

Figure 4:
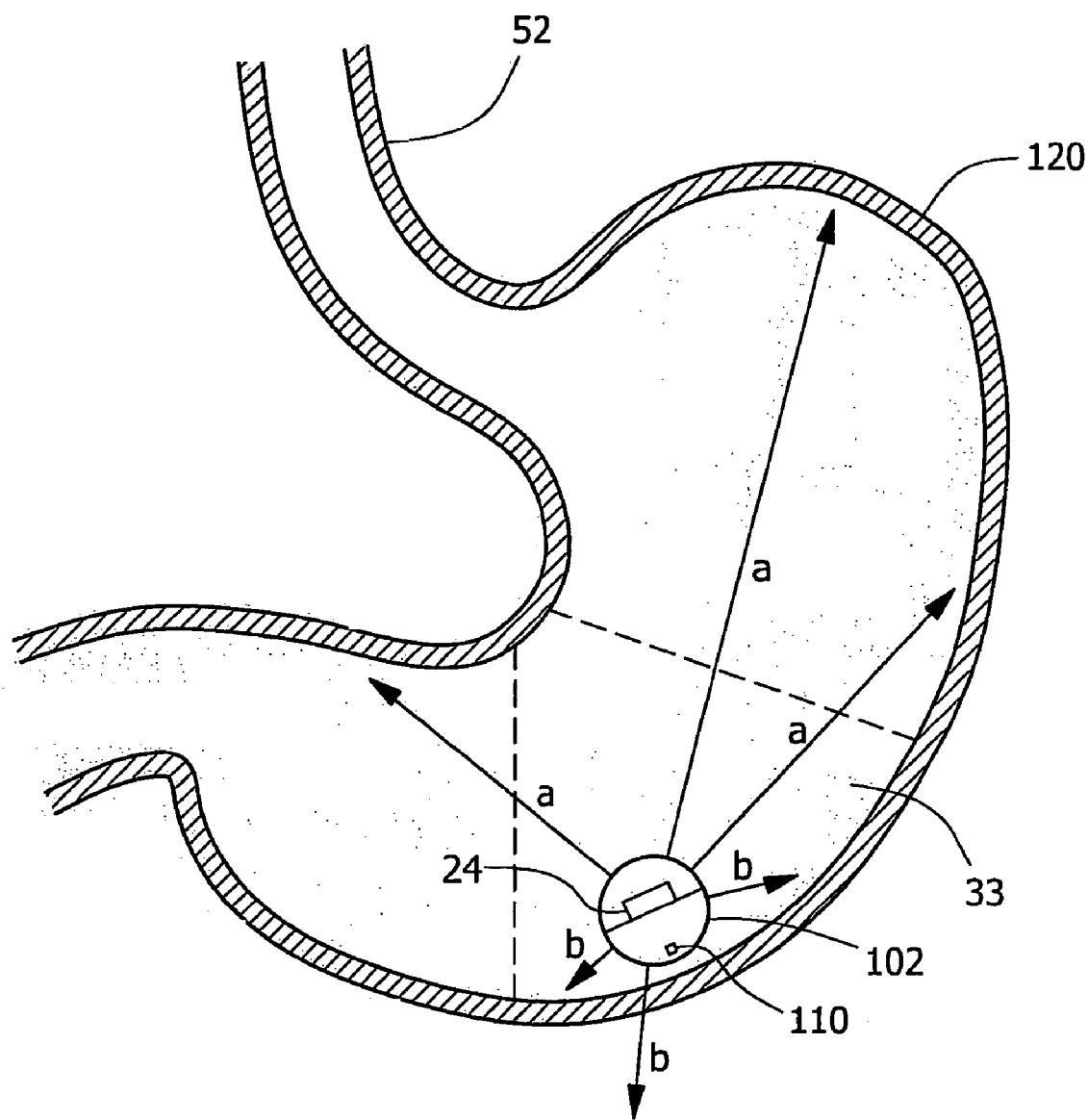
FIG. 4 schematically illustrates a device, for example, the device of FIG. 3 within a stomach, according to an embodiment of the present invention.

FIG. 4, to which reference is now made, depicts the spherical housing 102 of the device 100 within the antrum area 33 of a patient's stomach 120, according to an embodiment of the present invention. After passing through the esophagus 52, the appendage 104 has been dissolved, disintegrated, or removed, for example as described herein, and the device 100 is substantially spherical in shape, as defined by housing 102.

The now spherically shaped device 100 may pass through the relatively large and voluminous stomach 120. Changes of shapes to other shapes may be effected.

The spherical or substantially spherical shape may enable the device 100 to advance smoothly over a lumen wall, for example, glide over the typically moist (and thus substantially frictionless) surface of the stomach and to glide or roll over the ridges formed on the stomach wall. Thus, the motion of an imager 24 within the device 100 may be relatively smooth and continuous. The device 100, being substantially spherical, may be likely to rotate thereby altering the optical axis of the imager 24. However, the rotation of the optical axis in this case may be advantageous and may enable imaging of large parts of the stomach. As will be described herein below, the device 100 may be maneuvered into different areas of the stomach by controlled movement of the patient's body.

An optional ballast or weight 110 (also shown in FIG. 3A) may be placed in the housing 102 to ensure that the imager 24, for example, may maintain a specific orientation with respect to gravity, for example, such that the viewing window may face upwards. In this case, the images captured may tend to include a view oriented outward from the stomach wall of which device 100 is resting upon, as indicated by arrows "a", rather than oriented toward the wall on which the device 100 may be resting and may not generally capture images in directions marked as "b".

In embodiments where the device may image a "far wall" of a relatively voluminous lumen, the illumination sources typically output enough light so that the far wall may be adequately illuminated. Various methods of altering the amount of light output by the illumination units and/or adjusting the intensity in vivo, for example, in response to detection of the amount of light required or the amount of light received by the imager, may be used. For example, devices and methods for altering the light output from an imager are described in some embodiments in International Application publication number WO 03/009739 entitled "Apparatus and Method for Controlling Illumination or Imager Gain in an In-Vivo Imaging Device" published on 6 of February 2003, assigned to the assignee of the present invention, and incorporated herein by reference in its entirety.

Figure 5:
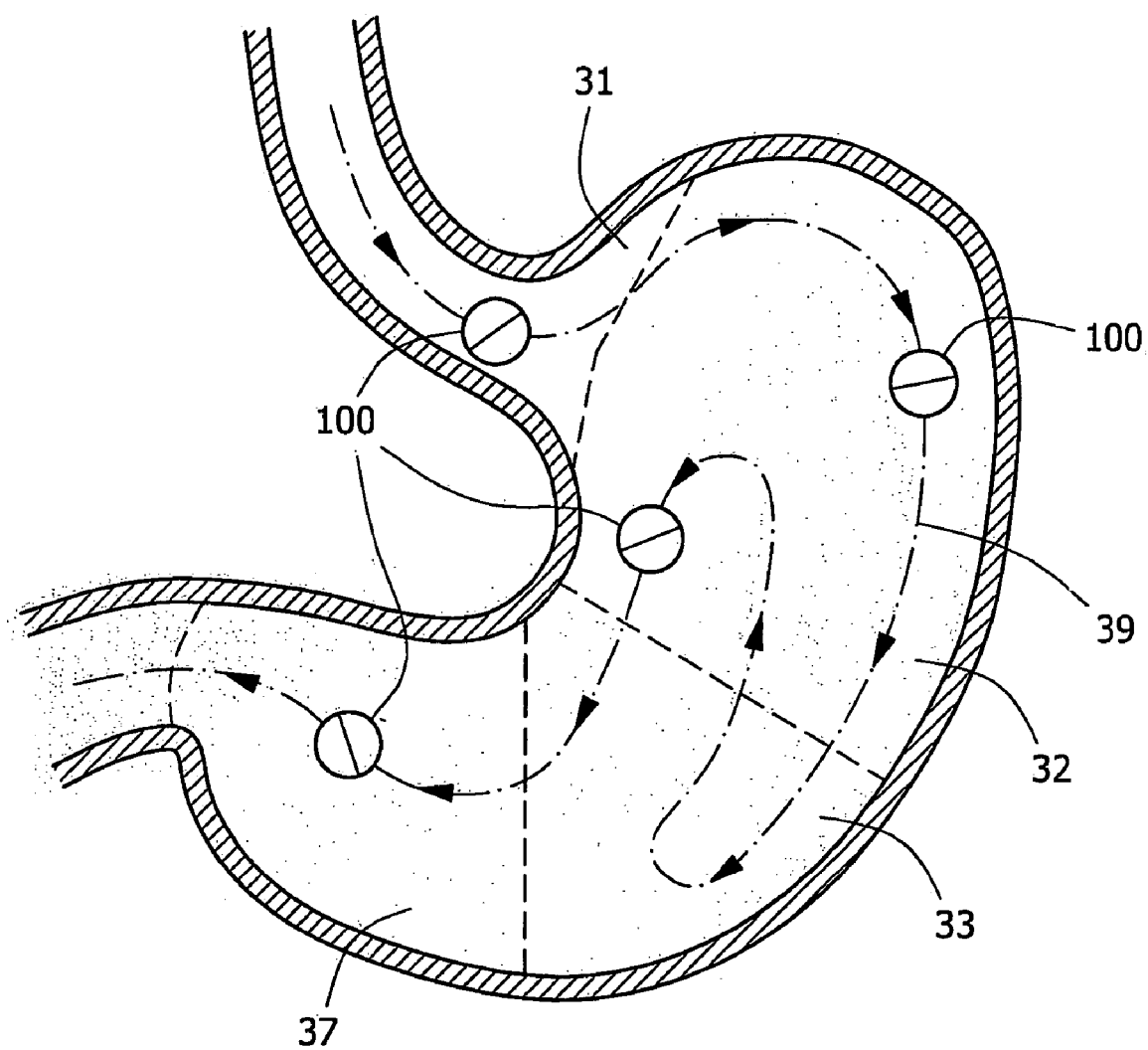
FIG. 5 illustrates the movement of the device of FIG. 3 through the stomach, according to an embodiment of the invention.

By adjusting the position and/or patient's body, for example, by moving the patient from side to side and rolling his body, the device 100 may be maneuvered into different areas of the stomach such as the cardia, fundus, antrum and the pyloric canal. Other body lumens may be so examined by use of a device as described herein and suitable manipulation of a patient's body. Controlled movement of the patient may allow for imaging different areas of the stomach over a period of, for example, 20-30 minutes. Other suitable periods may be used and other lumens may be imaged. FIG. 5 illustrates an example of the course that device 100 may take though the stomach by exemplary maneuvering of the patient's body. In one example, the device 100 may follow a track 39 that may covers most of the stomach body, including remote areas such as for example the cardia 31, fundus 32, antrum 33, and the pyloric canal 37. In one example, device 100 may discard its appendage 104 in the cardia 31 and continue through the stomach with sensing device 102. In other embodiments appendage 104 may be discarded in other locations.

Figure 6:
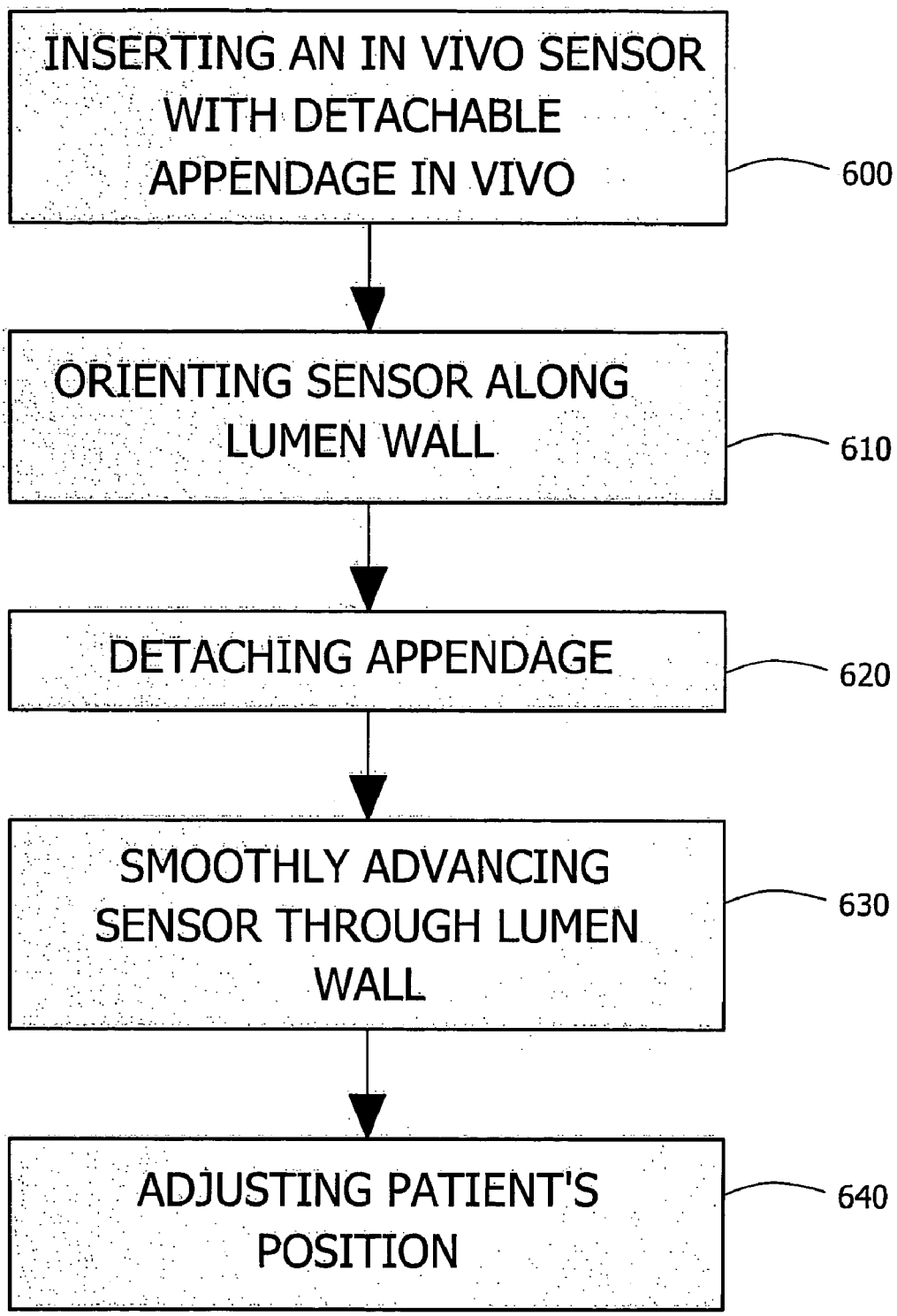
FIG. 6 is a flow chart depicting a method of in-vivo sensing according to an embodiment of the present invention.

Reference is now made to FIG. 6 that is a flow chart describing a method of in-vivo sensing according to an embodiment of the present invention. In operation 600 an in-vivo sensor with a detachable appendage may be provided. In some embodiments of the present invention, the in-vivo sensor may have a substantially spherical shape. According to one embodiment of the invention, the in-vivo sensor may be an imaging sensor, for example, an imaging sensor for imaging the upper GI tract. Other suitable sensors may be used as well and other suitable in-vivo lumens may be examined. In operation 610, the in-vivo sensor may be oriented with respect to the lumen wall, for example the esophagus wall or other suitable body lumen walls. The orientation with respect to the lumen wall may be provided in some embodiments of the present invention by providing an attached appendage. The appendage may, for example, extend the dimensions of the in-vivo device so as to provide an oblong shaped device that may not tumble in a relatively narrow lumen. In operation 620, the appendage may be detached from the in vivo sensor. The detachment may take place in some embodiments of the invention, upon entrance into a relatively voluminous lumen, for example, the stomach or large intestine. In operation 630, the in vivo sensor (detached from the appendage) may advance smoothly through, for example, a relatively voluminous lumen without, for example, tumbling. As such smooth continuous sampling of the lumen may be obtained. For example, in the case when the in-vivo sensor may be an image sensor, smooth, non-jerky image streams may be captured. In operation 640, a patient's position or orientation may be adjusted, for example, to help advance the in vivo sensor, systematically through the entire lumen. Other operations or series of operations may be used.

While the invention has been described with respect to a limited number of embodiments, it will be appreciated that many variations, modifications and other applications of the invention may be made which are within the scope and spirit of the invention.

The invention claimed is:

1. An ingestible imaging device comprising:
   an imaging device having a substantially spherical housing, said housing comprising a dome-shaped window through which a body lumen is illuminated and imaged; and
   a detachable appendage, wherein the housing and the detachable appendage form an oblong capsule shape when joined together such that the dome-shaped window forms an end of the oblong capsule shape.

2. The device according to claim 1 comprising:
   an illumination source; and
   a transmitter.

3. The device according to claim 2 wherein the illumination source has intensity that is adjustable in vivo.

4. The device according to claim 1 comprising a ballast weight.

5. The ingestible imaging device of claim 4, wherein an imaging axis of said imaging device is aligned with the oblong axis of the detachable appendage when joined together.

6. The device according to claim 4, wherein said imaging device comprises said ballast weight to maintain a specific orientation of the spherical housing with respect to gravity.

7. The device according to claim 4, wherein the ballast weight is positioned in said spherical housing such that at least upon detachment from said detachable appendage, said imaging device is directed to image an area of the body lumen opposite a portion of said body lumen upon which the spherical housing is resting.

8. The device according to claim 1 wherein the appendage includes a degradable material.

9. The device according to claim 8 wherein the degradable material is pH sensitive.

10. The device according to claim 1 wherein the appendage and the spherical housing are glued together.

11. The device according to claim 1 the appendage and the spherical housing are glued together with dissolvable glue.

12. The device according to claim 1 wherein the appendage comprises:
    an outer coating; and
    an internal filling.

13. The device according to claim 12 wherein the outer coating is semi-permeable.

* * * * *